United States Patent [19]

Urnovitz

[11] Patent Number: 4,698,420
[45] Date of Patent: Oct. 6, 1987

[54] ANTIBODY HYBRID MOLECULES AND PROCESS FOR THEIR PREPARATION

[75] Inventor: Howard B. Urnovitz, San Francisco, Calif.

[73] Assignee: Xoma Corporation, Berkeley, Calif.

[21] Appl. No.: 705,271

[22] Filed: Feb. 25, 1985

[51] Int. Cl.$^4$ .............................................. C07K 3/08
[52] U.S. Cl. .................................... 530/387; 530/389; 530/390; 530/402; 530/405; 424/85; 436/548; 436/547
[58] Field of Search ........................ 260/112 B, 112 R; 436/548, 547; 424/85; 530/387, 389, 402, 405

[56] References Cited

U.S. PATENT DOCUMENTS

| | | | |
|---|---|---|---|
| 4,340,535 | 7/1982 | Voisin et al. | 424/85 |
| 4,350,236 | 9/1982 | Masuho et al. | 530/390 |
| 4,350,626 | 9/1982 | Masuho et al. | 260/112.5 |
| 4,368,149 | 1/1983 | Masuho et al. | 424/85 |
| 4,379,145 | 4/1983 | Masuho et al. | 424/177 |
| 4,489,710 | 12/1984 | Spitler | 128/1 |

FOREIGN PATENT DOCUMENTS 0080401 6/1983 European Pat. Off. .............. 424/85

OTHER PUBLICATIONS

Wiels et al, "Properties of Immunotoxins Against Glycolipid . . . Lyomphoma", *Career Res.*, 44, pp. 129–133, 1984.
Carlson et al, "Protein Thiolation & Reversible Protein-Protein Conjugation", *Biochem. J.* 173, 1978, pp. 723–737.
Masuho et al, *J. Biochem.* 91, 1982, pp. 1583–1591.
S. M. Larson, et al., "Imaging of Melanoma with I-131-Labeled Monoclonal Antibodies", *Journal of Nuclear Medicine*, (1983), 24:123–129.
P. Midoux, et al., "Tumor Localization of Lewis Lung Carcinoma with Radiolabeled Monoclonal Antibodies", (1984), *Cancer Immunology Immunotherapy*, 18:19–23.
G. Qian, et al., "Circulating Monoclonal IgM Proteins in B Cell Chronic Lymphocytic Leukemia: Their Indentification, Characterization and Relationship to Membrane IgM", (1984), *The Journal of Immunology*, 133(6):3396–3400.
Vitetta et al., "Immunotoxins: A New Approach to Cancer Therapy", Science, 219, 1983, pp. 644–650.
Colombatti et al, "Selective Killing . . . Procedure", *J. Immunol.* 131(6) 1983, pp. 3091–3095.
Masuho et al, "Importance of Antigen-Binding . . . Antibody", *J. Biochem.*, 91, 1982, pp. 1583–1591.
Ramakrishnan et al, "Comparison of Selective . . . Monoclonal Antibodies", *Cancer Res.* 44, 1984, pp. 201–208.
M. J. Embleton, et al., "Antigenicity and Drug Susceptibility of Human Osteogenic Sarcoma Cells 'Escaping' a Cytotoxic Methotrexate–Albumin–Monoclonal Antibody Conjugate", (1984) *Brit. J. Cancer*, 49(3):559–565.
Hammersmith Oncology Group, "Antibody-Guided Irradiation of Malignant Lesions: Three Cases Illustrating a New Method of Treatment", (1984), *The Lancet*, 1(8392):1441–1443.
N. A. Kernan, et al., "Specific Inhibition of In Virto Lymphocyte Transformation by an Anti-Pan T Cell (gp67) Ricin A Chain Immunotoxin", (1984) *J. Immunol.*, 133(1):137–146.
R. A. Roth, et al., "Identification of a Lymphocyte Enzyme That Catalyzes Pentamer Immunoglobulin M Assembly", *Journal of Biological Chemistry*, (1981) 256(9):4633–9.
G. Kohler, et al., "Continuous Cultures of Fused Cells Secreting Antibody of Predefined Specificity", *Nature*, (1975), 256:495–497.
D. G. Gilliland, et al., "Antibody-Directed Cytotoxic Agents: Use of Monoclonal Antibody to Direct the Action of Toxin A chains to Colorectal Carcinoma Cells", *Proc. Natl. Acad. Sci.*, U.S.A., (Aug. 1980), 77:4539–4543.

*Primary Examiner*—John Kight
*Assistant Examiner*—Garnette D. Draper
*Attorney, Agent, or Firm*—Townsend and Townsend

[57] ABSTRACT

Antibodies which contain reduced sulfhydryl groups in proximity of the carboxyl terminal end of their heavy chain are coupled to another moiety which has an available sulfhydryl for forming a disulfide bond with the antibodies. IgM is a typical antibody which contains a suitable structure by virtue of its cysteine residue in proximity to the carboxyl terminal end of its heavy chain. A typical hybrid is formed with IgM and the A chain of a toxin such as ricin by the formation of a covalent disulfide bond therebetween. Use of antibodies having structures such as IgM result in hybrid formation in which the moiety joined to the antibody is site directed with respect to its bonding location on the antibody. Such hybrids have utility including in vivo therapeutic applications in which the functionality of the antibody is not deleteriously impaired by the moiety bonded thereto.

16 Claims, No Drawings

ANTIBODY HYBRID MOLECULES AND PROCESS FOR THEIR PREPARATION

BACKGROUND OF THE INVENTION

1. Field Of The Invention

This invention relates to antibody hybride. More particularly, it relates to antibody hybrids in which an organic moiety is covalently bonded to the antibody at a preselected location on the antibody so as to preserve the normal functionality of the antibody.

Antibody molecules exist in one of several classes. To date, five known classes (isotypes) in the higher vertebrates are designated as immunoglobulin (Ig) IgM, IgA, IgG, IgD, or IgE. The common structure for these immunoglobulins is a monomer composed of two heavy chains and two light chains. Heavy and light chains are covalently linked to each other by disulfide bonds and the two heavy chains are linked through disulfide bonds. Two of the immunoglobulin classes, IgM and IgA, exist naturally in a polymeric form. Polymers of the four chain structures are linked via the cysteine residue located in proximity to the carboxyl terminus on the constant region of the heavy chains.

The first step of polymerization of IgM or IgA is dimer formation. In the usual naturally occurring situation the penultimate carboxyl cysteine residue of two monomers are joined via a 20,000 dalton polypeptide joining or 'J' chain. After dimerization, pentamer formation of IgM is completed enzymatically by a thiol oxidoreductase. Richard A. Roth and Marion E. Koshland, "Identification of a Lymphocyte Enzyme That Catalyzes Pentamer Immunoglobulin M Assembly," *Journal of Biological Chemistry*, (1981) 256(9):4633-9. Polymerization of IgA is also initiated by J chain assembly. IgA molecules exist predominately as dimers and are not believed to utilize any other enzyme systems for further polymerization. Thus, homopolymers of monomer IgM or IgA are assembled in vivo via the cysteine residue near the carboxyl terminal end. The disulfide bonds at this position covalently link the monomers.

This invention presents a methodology for chemically linking carboxyl-terminal sulfhydryl residues of monoclonal antibodies to form hybrid molecules. These hybrid molecules are defined in the preferred embodiment as an antibody of the IgM or IgA class linked to another component including an antibody, enzyme, hormone, toxin or carrier protein (a protein which acts only as a delivery and amplification system for smaller molecular weight components) in which the carrier protein may contain a suitable labeling agent or a suitable cytotoxic agent.

2. Description Of The Prior Art

Pharmacokinetically/Therapeutically Active Moieties

The concept of cell population depletion in vivo is illustrated by the well known use of chemotherapeutic or cytotoxic agents in the treatment of cancer. The difficulties associated with such treatment are equally well known. The lack of cancer-specific cytotoxicity is a major difficulty, in that cytotoxic products kill both cancer cells and normal cells. (Due to normal cell toxicity, the therapeutic dosage of cytotoxic products has often been limited so that cancerous cells are not killed to a sufficient level to prevent or delay new cancerous growth.) Therefore, it is desirable to have a method of directing the cytotoxic agent directly to the tumor cells.

Tumor-associated antigens exist on the surface (or within the cytoplasm) of cancerous cells, and may also appear in the blood of the patient. Anti-tumor antibody may be found in a patient's blood, or the antibody may be generated by immunizing an animal with tumor cells.

Monoclonal antibodies (MoAb) obtained by the technology developed by Kohler and Milstein, "Continuous Cultures of Fused Cells Secreting Antibody of Predefined Specificity," *Nature*, (1975) 256:495-7, have a specificity toward cells bearing the antigen which the MoAb has been developed against. Although MoAbs have a common property of specificity for combination with tumor cells, they are not in themselves always cytotoxic to these cells. However, MoAbs may be combined with a cytotoxic agent such as a chemotherapeutic drug, a natural or artificial toxin or its fragment, or chelated radioisotope, or any combination of the above substances. The MoAb may thus be used as a carrier to deliver the cytotoxic agent directly to the tumor cell.

For example, Gilliland, et al. (PNAS 77:4539-4543, 1980) have conjugated either diphtheria or ricin toxin to a MoAb directed against a human colorectal carcinoma associated antigen, and either conjugate killed cells bearing the antigen in vitro.

The conventional chemotherapeutic drug methotrexate, combined with an anti-osteogenic sarcoma MoAb showed cytotoxicity in vitro to cultured osteogenic sarcoma cells (Embleton, et al., Brit. J. Can. 49(3):559-65, 1984).

A tumor-associated monoclonal antibody radiolabeled with $^{131}$I was used therapeutically on three cancer patients, and positive therapeutic results were obtained by the Hammersmith Oncology Group (Lancet 1(8392):1441-3, 1984).

Another in vitro illustration of cell population depletion is the removal of cell population subsets from bone marrow. In the case of leukemias and other blood cancers, selective removal of the stem cells in the bone marrow which produce the cancerous cells is a possible method of cure. MoAb directed against the appropriate tumor-associated antigen can be reacted with bone marrow which was removed from the patient. The resulting MoAb/leukemia complexes can be separated from the bone marrows and the "clean" bone marrow, containing the stem cells for the various normal blood cells free from cancerous cells, can be returned to the patient. See U.S. Pat. No. 4,489,710.

Kernan, et al. (J. Immunol. 133(1):137-46, 1984) found that an anti-pan T-cell MoAb conjugated to ricin A chain was an effective agent against immunocompetent T-lymphocytes in in vitro bone marrow, and "may be an effective agent for use in clinical bone marrow transplantation."

There are a number of prior art patents which are directed to the preparation of antibody hybrids similar to those of this invention. In general, such prior art describes the formation of a hybrid in which the antibody portion is an antibody fragment; where whole antibodies are used there is no direction or control as to the sites on the antibody where the attachment is made. U.S. Pat. No. 4,350,626 is typical of the antibody fragment approach, whereas U.S. Pat. No. 4,340,535 is directed to antibody hybrids which first involve the introduction of a linking group into the antibody by techniques which result in a random choice of reaction sites on the antibody. The moiety bonded to the linking group may have deleterious effects on the functionality of the antibody because of the reaction site. Other references in the above two categories include U.S. Pat. No. 4,368,149 and U.S. Pat. No. 4,379,145.

Diagnostic Moieties

MoAbs have an additional application besides therapy: that of serving as a director of diagnostic moieties. By labeling a cell population such as tumor cells with a detection agent, the cell population in question can be identified with an appropriate scanning device. The major detection systems, either in current use or having potential value, include colorimetric, radioactive, colloid metals, and fluorochromes.

Numerous studies exist in which radiolabeled MoAbs have been used in vivo to image malignancies both in humans and animal systems. For example, Larson, et al. (J. Nucl. Med. 24:123–9, 1983) have imaged human melanoma lesions in both animals and humans with an anti-melanoma MoAb labeled with 131I.

Numerous MoAb based products are in current commercial use as in vitro diagnostic systems for the detection of isotopes. For example, there is a detection kit for Human Chorionic Gonadotropin using a MoAb bound to peroxidase for an EIA assay. Also, there is a detection kit for digoxin which utilizes a radiolabeled MoAb in an RIA assay.

SUMMARY OF THE INVENTION

In accordance with the present invention an antibody hybrid is provided which comprises an antibody having a cysteine residue in proximity to (usually adjacent) the carboxyl terminal end of its heavy chain and an organic moiety having an available sulfhydryl for forming a disulfide bond, the sulfhydryl of said cysteine residue being bonded to said available sulfhydryl.

The hybrid is prepared by reacting to form a covalent disulfide bond therebetween (a) the monomeric form of an antibody having a cysteine residue in proximity to the carboxyl terminal end of its heavy chain with (b) an organic moiety having an available sulfhydryl group, one of the sulfhydryl group of the cysteine residue of said antibody and said organic moiety being activated and the other one of the sulfhydryl groups being in reduced sulfhydryl form.

DETAILED DESCRIPTION OF THE PREFERRED EMBODIMENTS

The present invention utilizes the natural tendency of certain classes of antibodies to polymerize via their sulfhydryl residues on the carboxyl terminal end of their heavy chains. By mildly reducing intermonomeric disulfide bonds, the carboxyl terminal sulfhydryl groups can be activated to react with free sulfhydryl residues on a second protein or other organic moiety. Conversely, the free reduced sulfhydryl residues of the antibody's carboxyl terminal end can be reacted with activated sulfhydryl groups of the second protein or other organic moiety. These reactions may be illustrated:

A. Antibody—S′—X +P—SH Antibody —S—S′—P

B. Antibody—S′H +P—S—X Antibody —S′—S—P where S′ is part of the carboxyl terminal cysteine residue of the antibody, X is a leaving group, S is the attachment sulfur atom of the second protein (or other organic moiety) P.

Some of the advantages of the invention over previous methodologies are:

(1) the immunoglobulin does not require enzyme fragmentation, (2) no special precautions for protecting the binding region are necessary since the binding region of the antibody is unaffected by this procedure, and (3) in the case when pyridine-2-thione is released as a byproduct, the reaction kinetics can be followed spectrophotometrically.

In the reactions, mild reduction is utilized with appropriate reagents being selected so that only intermolecular bonds are broken between monomers of the antibody, and the breaking of intramolecular bonds within the monomers is avoided. Typical mild reducing agents for such purposes include dithiothreitol, mercaptoethanol and cysteine, at dilute concentrations of appropriate pH at low temperature.

The moiety to be bonded to the antibody can be any organic moiety which has an available sulfhydryl group for forming a disulfide bond with the antibody. The moiety may be selected from proteins having an available sulfur group in which the sulfhydryl group is naturally occurring or the sulfhydryl may be added to the protein as part of a linking group as described, for example, in U.S. Pat. No. 4,340,535. The protein may be a labeled protein having a radioactive, colorimetric, colloidal metal or fluorochrome type of a label. Hybrids formed from labeled proteins will typically have utility in in vivo and in vitro diagnostic applications.

A preferred group of organic moieties include toxins in which the A chain of the toxin is linked to the antibody. Examples of such toxins include diphtheria (bacterial origin) and ricin (plant origin). Other alternatives for the organic moiety may be a chemotherapeutic drug or agent such as methotrexate, which results in a hybrid having in vivo or in vitro therapeutic utility, for example in the treatment of cancer. As will be demonstrated by actual example, the organic moiety can be another antibody.

In the above reaction schemes illustrated by equations, the leaving group X is usually introduced by reaction of either the antibody or organic moiety to be activated with an organic activator of the formula $X_1$—S—S—$X_2$, wherein $X_1$ and $X_2$ are selected from pyrid—2—yl, pyrid-4-yl and phenyl, in which the pyridyl groups may be substituted by a member selected from alkyl which may contain for example 1-10 carbon atoms, halogen and carboxylic acid, and the phenyl group may be substituted by a member selected from nitro and carboxylic acid.

Preferably the reaction is carried out in the presence of a substantial molar excess of said organic activator in accordance with the following equation:

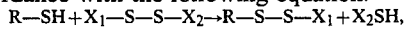
R—SH+$X_1$—S—S—$X_2$→R—S—S—$X_1$+$X_2$SH, wherein R is the residue of the antibody or the organic moiety and $X_1$ and $X_2$ are as defined above. The reaction will usually be executed in a suitable buffer solution at a pH of about 4–10 and at temperatures ranging from 0° C. to ambient.

The invention encompasses the use of polyclonal and monoclonal (including genetically manipulated) antibodies with monoclonal antibodies being preferred. The feasibility of utilizing a monoclonal IgM in the present invention is indicated by Patrick Midoux, et al., "Tumor Localization of Lewis Lung Carcinoma with Radiolabeled Monoclonal Antibodies," *Cancer Immunology Immunotherapy*, (1984) 18:19–23, in which radiolabeled monoclonal IgM is studied in an in vivo environment. The work reported by Guan-Xiang Qian, et al., "Circulating Monoclonal IgM proteins in B Cell Chronic Lymphocytic Leukemia: Their Identification, Characterization and Relationship to Membrane IgM", *The Journal of Immunology*, (1984) Vol. 133, No. 6, pages 3396–3400, further illustrates the feasibility of the present approach in reporting the existence of IgM in vivo as a monomer dissolved in the blood of the subjects being studied.

EXPERIMENTAL EXAMPLE 1

The following example illustrates the application of joining the reduced form of an IgM antibody to an organic moiety that does not have a readily available sulfhydryl group for conjugation. The moiety selected for this example is an $IgG_1$ monoclonal antibody An effective means of coupling components to the reduced cysteine group of antibody monomers is through sulfhydryl residues. If there are no accessible residues on the component, reactive sulfhydryl residues are introduced via modifying agents. In this example, activated sulfhydryl residues were introduced into the $IgG_1$ monoclonal anti-DNP (dinitrophenol) antibody via the modifier SPDP (3-[2-Pyridyldithio]proprionic Acid N-Hydroxysuccinimide Ester). SPDP (700 ug/ml absolute ethanol) is added dropwise to a stirring solution of the $IgG_1$ antibody (7 mg/ml of coupling buffer, composed of 0.1M $NaPO_4$, 0.1M NaCl, pH 7.7). The solution is stirred at room temperature for 30 minutes followed by passage over a desalting column (equilibrated with coupling buffer).

After the antibody is modified, purified monoclonal anti-DNP IgM antibody (7 mg/ml) is stirred at room temperature with 2–10 mM DTT (dithiothreitol). The solution is periodically bubbled with inert nitrogen gas. After 1 hour, the solution is passed over a desalting column (equilibrated with coupling buffer) and passed immediately into the gently stirring solution of SPDP modified $IgG_1$ antibody. The solution is stirred at room temperature until the OD at 343 nanometers reaches a plateau (1 to 24 hours). In the preferred embodiment, the solution is then concentrated, dialyzed against buffer and separated on a sizing column to remove conjugates from unreacted enzyme. The efficiency of coupling can be calculated from the molar release of pyridine-2-thione during the reaction (absorption coefficient $=8.08\times 10^3$ $M^{-1}.cm^{-1}$ at 343 nanometers).

The above technique works equally well with IgA monomers substituted for IgM in this example.

EXAMPLE 2

Antibody-antibody hybrids can also be constructed by activating CTCR (carboxyl terminal cysteine residue) on the IgM antibody monomers. Using the same procedure as in Example 1, the reduced sulfhydryl residues on the IgM antibody monomer are activated by passaging the reduced monomer over a desalting column (equilibrated with coupling buffer) and immediately adding dipyridyl disulfide (final concentration $=1$ mM in coupling buffer) After the SPDP modified $IgG_1$ antibody is exposed to a reducing agent, the solution is passaged over a desalting column directly into a stirring solution of the activated IgM antibody monomer. Reaction and purification procedures are identical to those cited in Example 1.

EXAMPLE 3

To illustrate the coupling of other types of organic moieties, which have natural sulfhydryl available for coupling, in this example the A chain of the toxin ricin was isolated. Anti-DNP IgM antibody was reduced and activated as in Example 2. Reduced ricin A chain was added to the stirring solution of activated IgM and allowed to react at room temperature for one hour. After dialysis against phosphate buffer, the conjugates were analyzed by gel electrophoresis and enzyme immuno- assay.

EXAMPLE 4

An alternative conjugation scheme for the components described in Example 3 is illustrated in this example. In this example, the sulfhydryl residues on ricin A chain are activated and reacted with the reduced form of the antibody as described in Example 1. Ricin A chain was mixed with dipyridyl disulfide (1 mM) for 30 minutes at room temperature and passaged over a desalting column. The reduced form of the anti-DNP IgM antibody was added to the mixture and allowed to stir at room temperature for 30 minutes. The products were analyzed by gel electrophoresis and immunoblots.

What is claimed is:

1. A method for preparing an antibody hybrid molecule by forming a covalent disulfide bond between a sulfhydryl group on an organic moiety and a intermolecular sulfhydryl group found on the carboxyl terminal cysteine residue of the heavy chain of the monomeric form of an antibody of class IgA of IgM, said method comprising the steps of:

(1) selecting an polymeric antibody of interest, said antibody selected from the group consisting of class IgA or IgM antibodies;

(2) activating a sulfhydryl group found on the carboxyl terminal cysteine residue of the heavy chain of the monomeric form of said anitbody by mild reduction, wherein the mild reduction breaks a intermolecular polymer-forming disulfide bond without breaking intramolecular bonds; and (3) conjugating said antibody monomer to a moiety of interest by way of a disulfide bond consisting essentially of a bond formed between said activated sulfhydryl group and a free sulfhydryl group on said moiety.

2. A method according to claim 1, wherein said mild reduction is accomplished by exposing said polymeric antibody to a concentration of dithiothreitol.

3. A method according to claim 2, wherein said concentration of dithiothreitol is 2mM to 10mM.

4. A method according to claim 2, wherein said polymeric antibody is exposed to said concentration of dithiothreitol in the presence of nitrogen.

5. A method according to claim 1, wherein said mild reduction is accomplished by exposing said polymeric antibody to a concentration of mercaptoethanol.

6. A method according to claim 1, wherein said mild reduction is accomplished by exposing said polymeric antibody to a concentration of cysteine.

7. A method according to claim 1, wherein said organic moiety is selected from toxins, labeled proteins, antibodies and chemotherapeutic drugs.

8. A method according to claim 1, wherein said organic moiety is a radio labeled protein.

9. A method according to claim 1, wherein said organic moiety is the A chain of a toxin.

10. A method according to claim 9, wherein said A chain is ricin A chain.

11. An antibody hybrid comprising an organic moiety and an antibody monomer of class IgA or IgM, wherein said organic moiety is bound to said antibody monomer by a disulfide bond consisting essentially of a bond formed between an activated intermolecular sulfhydryl group found on the carboxyl terminal cysteine residue of the heavy chain of said antibody and a free sulfhydryl group on said moiety.

12. An antibody hybrid according to claim 11, wherein said hybrid is produced by the method according to claim 1.

13. A hybrid according to claim 11, wherein said organic moiety is selected from toxins, ladeled proteins, antibodies and chemotherapeutic drugs.

14. A hybrid according to claim 11, wherein said organic moiety is a radio labeled protein.

15. A hybrid according to claim 11, wherein said organic moiety is the A chain of a toxin.

16. A hybrid according to claim 15, wherein said A chain is ricin A chain.

* * * * *